United States Patent
Takeuchi et al.

(10) Patent No.: US 10,221,382 B2
(45) Date of Patent: Mar. 5, 2019

(54) HOLLOW MICROFIBER

(71) Applicant: THE UNIVERSITY OF TOKYO, Tokyo (JP)

(72) Inventors: Shoji Takeuchi, Tokyo (JP); Hiroaki Onoe, Tokyo (JP); Shigenori Miura, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/312,561

(22) PCT Filed: May 20, 2015

(86) PCT No.: PCT/JP2015/064524
§ 371 (c)(1),
(2) Date: Nov. 18, 2016

(87) PCT Pub. No.: WO2015/178427
PCT Pub. Date: Nov. 26, 2015

(65) Prior Publication Data
US 2017/0130184 A1    May 11, 2017

(30) Foreign Application Priority Data
May 20, 2014 (JP) ................................. 2014-104763

(51) Int. Cl.
| C12M 1/12 | (2006.01) |
| B01D 69/08 | (2006.01) |
| B01D 69/12 | (2006.01) |
| B01D 69/14 | (2006.01) |
| B01D 17/00 | (2006.01) |

(52) U.S. Cl.
CPC ........... *C12M 25/10* (2013.01); *B01D 69/081* (2013.01); *B01D 69/085* (2013.01); *B01D 69/12* (2013.01); *B01D 69/144* (2013.01); *C12M 25/12* (2013.01); *B01D 17/08* (2013.01); *B01D 2323/42* (2013.01)

(58) Field of Classification Search
CPC ...................................................... C12M 1/12
See application file for complete search history.

(56) References Cited

U.S. PATENT DOCUMENTS
2012/0301963 A1   11/2012   Takeuchi et al.

FOREIGN PATENT DOCUMENTS
| WO | 2011/046104 A1 | 4/2011 |
| WO | 2011/046105 A1 | 4/2011 |

OTHER PUBLICATIONS

International Search Report dated Aug. 18, 2015 corresponding to International Patent Application No. PCT/JP2015/064524, filed on May 20, 2015; 2 pages.
Hirayama, Kayoko et al., "3d microfluidics formed with hydrogel sacrificial structures," IEEE 25$^{th}$ International Conference on Micro Electro Mechanical Systems (MEMS)(2012): Abstract, only Internet Search downloaded Nov. 18, 2016; 3 pages.
Lee, Kwang Ho et al., "Synthesis of Cell-Laden Alginate Hollow Fibers Using Microfluidic Chips and Microvascularized Tissue-Engineering Applications," *Small* (published online Mar. 19, 2009); 5(11):1264-1268.
Onoe, Hiroaki et al., "Bottom Up Soshiki Kogaku," (Non-English) *Journal of the Society for Bioscience and Bioengineering*, Japan (Apr. 25, 2014), with English translation of relevant section, p. 163, right column, line 6 from the bottom to p. 165, left column, line 18.
Onoe, Hiroaki et al., "Metre-long cell-laden microfibers exhibit tissue morphologies and functions," *Nature Materials* (published online Mar. 31, 2013); 12:584-590.

*Primary Examiner* — Bin Shen
(74) *Attorney, Agent, or Firm* — Mintz, Levin, Cohn, Ferris, Glovsky and Popeo, P.C.

(57) ABSTRACT

The present invention relates to a hollow microfiber comprising (1) one or more cell-adhesive layers having a cell-adhesive hydrogel, (2) an outer shell layer having a high-strength hydrogel that covers the outer periphery of the cell-adhesive layer that is positioned farthest from the center axis among the one or more cell-adhesive layers, and (3) a cell layer that covers the inner periphery of the cell-adhesive layer that is positioned closest to the center axis among the one or more cell-adhesive layers. The present invention also relates to a method of manufacturing the hollow microfiber and a kit for carrying out the manufacturing method.

17 Claims, 5 Drawing Sheets

FIG. 1
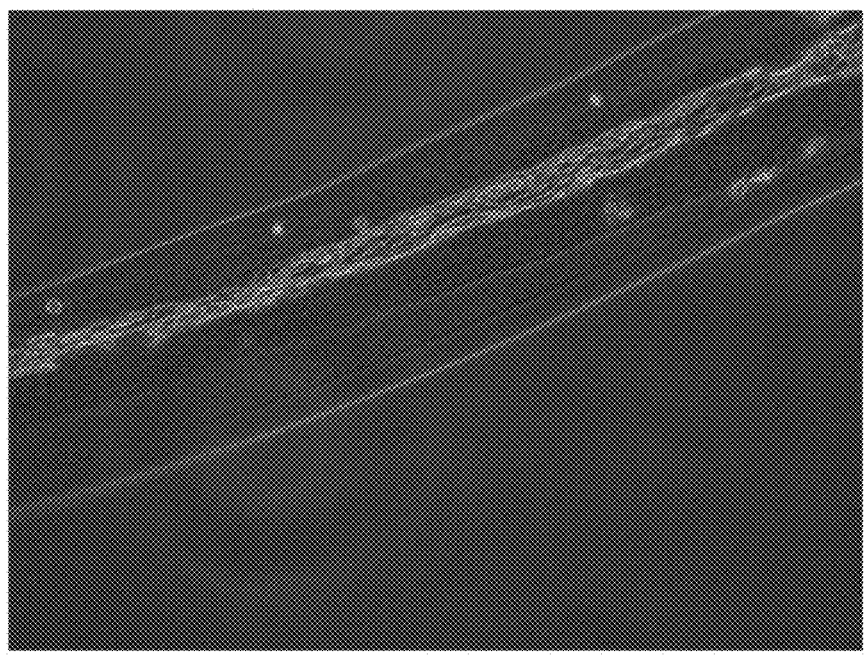
FIG. 2
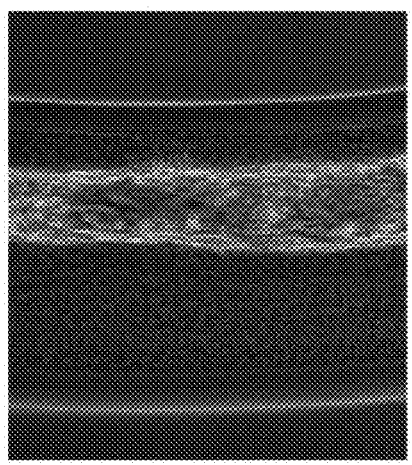
BEFORE REMOVAL OF
HIGH-STRENGTH HYDROGEL
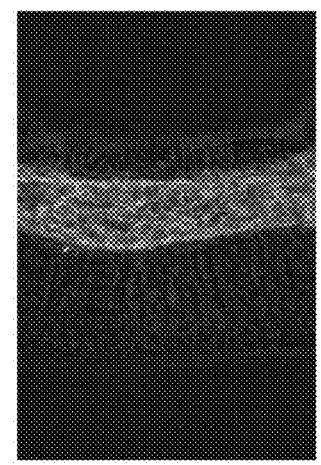
AFTER REMOVAL OF
HIGH-STRENGTH HYDROGEL FIG. 4
t = 0 sec
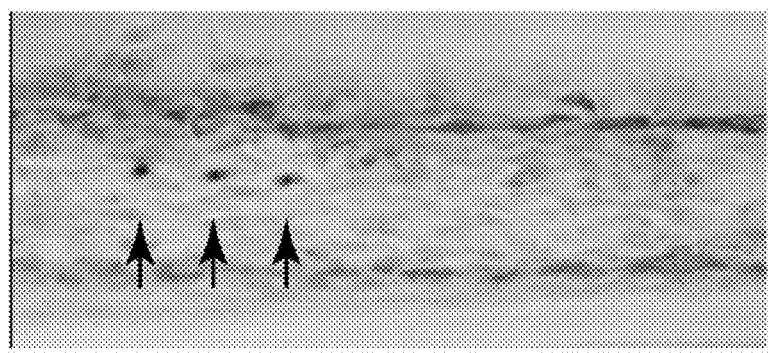
t = 18 sec
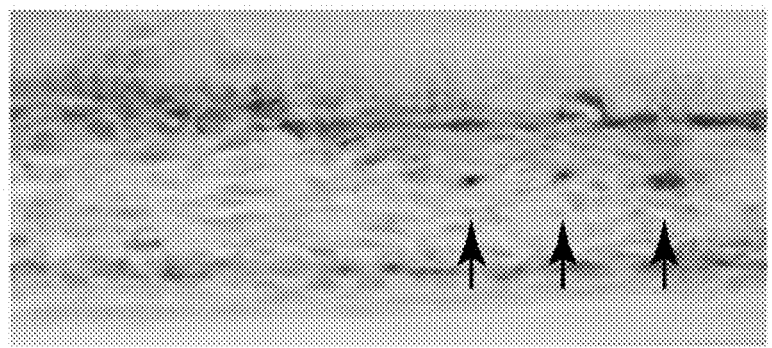

HOLLOW MICROFIBER

CROSS-REFERENCES TO RELATED APPLICATIONS

This application is a U.S. national application under 35 U.S.C. § 371 of International Application No. PCT/JP2015/064524 filed May 20, 2015, which claims priority benefit to Japanese Patent Application No. 2014-104763 filed May 20, 2014, each of which is incorporated in its entirety herein by reference thereto.

TECHNICAL FIELD

The present invention relates to a hollow microfiber comprising a cell layer, a method for producing the hollow microfiber, and a kit for carrying out the method for producing the microfiber.

BACKGROUND ART

In the field of regenerative medical research aimed at the replacement of organs and tissues, there is a need for the development of a technology for constructing artificial three-dimensional cellular tissue. A microfiber is known to be able to serve as the basic units for forming such three-dimensional cellular tissue, and the microfiber has a core-shell structure in which a fiber core (core portion), obtained by mixing cells into an extracellular matrix component in the form of collagen or fibrin, is covered with an outer shell portion such as an alginate gel (Patent Document 1). The microfiber has sufficient mechanical strength for handling, and enables the construction of three-dimensional cellular tissue while maintaining cell function. In addition, the microfiber can be prepared using various types of cells, including nerve cells, muscle cells, fibroblasts and epithelial cells.

The development of technology for artificially constructing internal tissues having a luminal structure such as blood vessels and lymph ducts is also sought in the field of regenerative medical research. A conventionally known method for producing blood vessel-like structures from cells comprises preparing long, narrow openings in a mass of collagen gel by molding and then culturing cells such as vascular endothelial cells in the inner wall thereof.

It is known that when vascular endothelial cells are introduced into the core portion of the aforementioned microfiber and cultured with an extracellular matrix component, the vascular endothelial cells spontaneously forms lumen within the microfibers (Non-Patent Document 1).

PRIOR ART DOCUMENTS

Patent Documents

Patent Document 1: International Publication No. WO 2011/046105

Non-Patent Documents

Non-Patent Document 1: Nature Materials, Vol. 12, pp. 584-590, 2013

SUMMARY OF THE INVENTION

Problems to be Solved by the Invention

However, in the case of having introduced vascular endothelial cells and an extracellular matrix component into the core portion of a microfiber having a core-shell structure and culturing the cells, the cell layer was formed randomly and it was difficult to form a continuous luminal structure having a constant length.

Thus, an object of the present invention is to provide a microfiber capable of transporting a liquid in which a continuous luminal structure having a constant length has been formed by a cell layer.

Means for Solving the Problems

As a result of conducting extensive studies in consideration of the aforementioned problems, the inventors of the present invention found that, by passing a cell suspension through the hollow portion of a microfiber composed of a tubular cell-adhesive layer containing a cell-adhesive hydrogel and an outer shell layer containing a high-strength hydrogel that covers the outer periphery of the cell-adhesive layer followed by culturing the cells, a continuous cell layer can be formed that covers the inner periphery of the cell-adhesive layer, thereby leading to completion of the present invention.

Namely, the present invention has the aspects indicated below.

[1] A hollow microfiber, comprising:
(1) one or more cell-adhesive layers containing a cell-adhesive hydrogel,
(2) an outer shell layer containing a high-strength hydrogel that covers the outer periphery of the cell-adhesive layer located farthest from the central axis among the one or more cell-adhesive layers, and
(3) a cell layer that covers the inner periphery of the cell-adhesive layer located closest to the central axis among the one or more cell-adhesive layers.

[2] The hollow microfiber described in [1], wherein the cell-adhesive hydrogel is selected from the group consisting of chitosan gel, collagen gel, gelatin, peptide gel, laminin gel, fibrin gel and mixtures thereof.

[3] The hollow microfiber described in [1] or [2], wherein the high-strength hydrogel is an alginate gel or agarose gel.

[4] The hollow microfiber described in any of [1] to [3], wherein the outer diameter of the outer shell layer is 20 μm to 500 μm.

[5] The hollow microfiber described in any of [1] to [4], wherein the cells that compose the cell layer are selected from the group consisting of vascular endothelial cells, lymphatic endothelial cells and renal tubular cells.

[6] The hollow microfiber described in any of [1] to [5], wherein at least one of the one or more cell-adhesive layers contains cells differing from the cells of the cell layer.

[7] The hollow microfiber described in any of [1] to [6], wherein the number of the one or more cell-adhesive layers is one layer.

[8] A hollow microfiber obtainable by removing the outer shell layer from the hollow microfiber described in any of [1] to [7].

[9] A microfiber in which the hollow portion of the hollow microfiber described in any of [1] to [7] is filled with a suspension of the cells that compose the cell layer.

[10] The microfiber described in [9], wherein the cell suspension is prepared by suspending the cells in a liquid selected from the group consisting of polyethylene glycol, glycerol, alginate ester, dextran and mixtures thereof.

[11] A microfiber obtainable by removing the outer shell layer from the microfiber described in [9] or [10]. [12] A method for producing a microfiber comprising:

(1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, (3) a cell layer that covers the inner periphery of the cell-adhesive layer located closest to the central axis among the one or more cell-adhesive layers, and (4) a cell suspension that fills a hollow portion; wherein, the method comprises the following steps:

(i) forming a laminar flow of the cell suspension, (ii) forming one of more laminar flows of solutions for preparing the cell-adhesive hydrogel that cover the outer periphery of the laminar flow of the cell suspension, (iii) forming a laminar flow of a solution for preparing a high-strength hydrogel that covers the outer periphery of the laminar flow of the solution for preparing the cell-adhesive hydrogel located farthest from the central axis among the laminar flows of the solutions for preparing the cell-adhesive hydrogel, (iv) gelling the solution for preparing the high-strength hydrogel to form an outer shell layer that contains the high-strength hydrogel, (v) gelling the solutions for preparing the cell-adhesive hydrogel to form the one or more cell-adhesive layers containing the cell-adhesive hydrogel, and (vi) culturing the cells in the cell suspension to form the cell layer.

[13] A method for producing a microfiber comprising:

(1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, (3) a cell layer that covers the inner periphery of the cell-adhesive layer located closest to the central axis among the one or more cell-adhesive layers, and (4) a cell suspension that fills a hollow portion; wherein, the method uses a coaxial microfluidic device provided with:

a line for introducing the cell suspension, one or more lines for introducing solutions for preparing the cell-adhesive hydrogel that are coaxial to the line for introducing the cell suspension, a line for introducing the solution for preparing the high-strength hydrogel that is coaxial to the line for introducing the cell suspension and the one or more lines for introducing solutions for preparing the cell-adhesive hydrogel, a region for gelling the solution for preparing the high-strength hydrogel, and a region for gelling the solutions for preparing the cell-adhesive hydrogel; and, the method comprises the following steps:

(i) forming a laminar flow of the cell suspension by injecting the cell suspension from the line for introducing the cell suspension, (ii) forming one or more laminar flows of the solutions for preparing the cell-adhesive hydrogel that cover the outer periphery of the laminar flow of the cell suspension by injecting the solutions for preparing the cell-adhesive hydrogel from the one or more lines for introducing solutions for preparing the cell-adhesive hydrogel, (iii) forming a laminar flow of the solution for preparing the high-strength hydrogel that covers the outer periphery of the laminar flow of the solution for preparing the cell-adhesive hydrogel located farthest from the central axis among the one or more laminar flows of the solutions for preparing the cell-adhesive hydrogel by injecting the solution for preparing the high-strength hydrogel from the line for introducing the solution for preparing the high-strength hydrogel, (iv) gelling the solution for preparing the high-strength hydrogel by passing an aggregate of the laminar flows formed in steps (i) to (iii) through the region for gelling the solution for preparing the high-strength hydrogel to form an outer shell layer containing the high-strength hydrogel, (v) gelling the solutions for preparing the cell-adhesive hydrogel by passing an aggregate of the laminar flows formed in steps (i) to (iii) through the region for gelling the solution for preparing the cell-adhesive hydrogel to form cell-adhesive layers containing the cell-adhesive hydrogel, wherein this step is carried out before or after step (iv) or simultaneous to step (iv), and (vi) culturing the cells in the cell suspension to form the cell layer.

[14] The method for producing the microfiber described in [12] or [13], wherein the cell suspension is prepared by suspending cells in a liquid selected from the group consisting of polyethylene glycol, glycerol, alginate ester, dextran and mixtures thereof.

[15] The method for producing the microfiber described in any of [12] to [14], wherein the cell density in the cell suspension is $1.0 \times 10^6$ cells/ml to $1.0 \times 10^8$ cells/mL.

[16] The method for producing the microfiber described in any of [12] to [15], wherein the solution for preparing the cell-adhesive hydrogel and the solution for preparing the high-strength hydrogel are gelled under different conditions.

[17] The method for producing the microfiber described in any of [12] to [16], wherein the cell-adhesive hydrogel is selected from the group consisting of chitosan gel, collagen gel, gelatin, peptide gel, laminin gel, fibrin gel and mixtures thereof.

[18] The method for producing the microfiber described in any of [12] to [17], wherein the high-strength hydrogel is an alginate gel or agarose gel.

[19] The method for producing the microfiber described in any of [12] to [18], wherein the cell-adhesive hydrogel is a collagen gel, and the high-strength hydrogel is an alginate gel.

[20] A microfiber produced by the method described in any of [12] to [19].

[21] A microfiber obtainable by removing the outer shell layer from the microfiber described in [20].

[22] A method for producing a hollow microfiber comprising:

(1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, and (3) a cell layer that covers the inner periphery of the cell-adhesive layer located closest to the central axis among the one or more cell-adhesive layers; wherein, the method comprises a step of removing the cell suspension from the microfiber produced by the method described in any of [12] to [19].

[23] A hollow microfiber produced by the method described in [22].

[24] A hollow microfiber obtainable by removing the outer shell layer from the hollow microfiber described in [23].

[25] A kit for carrying out the method for producing a microfiber described in any of [12] to [19], containing:

(i) a solution for preparing a cell-adhesive hydrogel that forms a cell-adhesive hydrogel by gelling, (ii) a solution for preparing a high-strength hydrogel that forms a high-strength hydrogel by gelling, (iii) a cell suspension, and (iv) a manual for producing the microfiber.

Effects of the Invention

According to the present invention, a microfiber capable of transporting a liquid can be provided which has a constant length and in which a continuous luminal structure has been formed by a cell layer. This microfiber is able to function as an alternative to a luminal structure such as a blood vessel or lymph duct in the body, and can be used in fields such as regenerative medicine. In addition, the microfiber of the present invention can be incorporated in three-dimensional tissue after having been produced. For example, the microfiber of the present invention produced using vascular endothelial cells can be incorporated in three-dimensional tissue to easily fabricate a vascular network.

BRIEF DESCRIPTION OF THE DRAWINGS

FIG. 1 is a drawing indicating the appearance of a microfiber produced according to Example 1(a).

FIG. 2 is a drawing indicating the appearance of a microfiber following removal of the outer shell layer thereof with alginate lyase. The image on the left shows the microfiber before removal of the outer shell layer, while the image on the right shows the microfiber after removal of the outer shell layer.

FIG. 4 is a drawing indicating that the hollow portion of a microfiber produced according to Example 1 is able to transport liquid.

DESCRIPTION OF EMBODIMENTS

Figure 3:
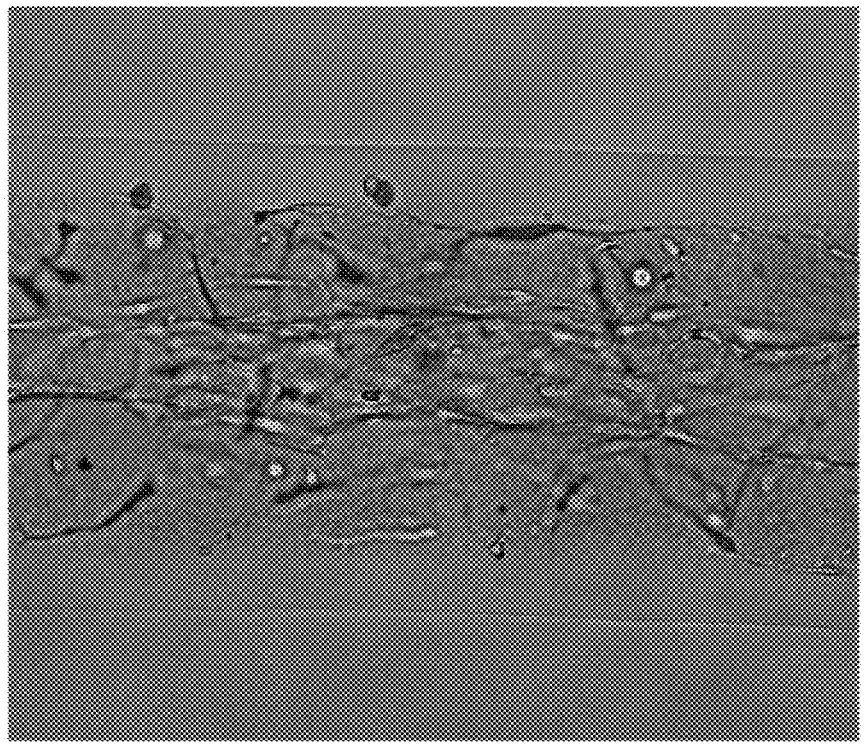
FIG. 3 is a drawing indicating a microfiber produced by co-culturing vascular endothelial cells and vascular smooth muscle cells according to Example 2.

One aspect of the present invention is a hollow microfiber comprising: (1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, and (3) a cell layer that covers the inner periphery of the cell-adhesive layer located closest to the central axis among the one or more cell-adhesive layers.

In the present description, although a "microfiber" refers to a fibrous structure having an outer diameter of, for example, about 10 μm to 1 mm, the outer diameter is not particularly limited to the aforementioned range. The cross-sectional shape in the direction perpendicular to the central axis may be circular, oval or in the shape of a polygon such as a quadrangle or pentangle. The cross-sectional shape is preferably circular.

In the present description, a "hollow microfiber" refers to that having the form of a microfiber while also having a hollow portion that passes along the central axis thereof. The cross-sectional shape of the hollow microfiber of the present invention is preferably circular. Although there are no particular limitations on the diameter of the hollow portion in that case, it is preferably 5 μm to 500 μm, more preferably 5 μm to 400 μm, even more preferably 5 μm to 300 μm, and particularly preferably 5 μm to 200 μm.

Although there are no particular limitations on the inner diameter of the outer shell layer of the hollow microfiber of the present invention, it is preferably 10 μm to 500 μm and more preferably 10 μm to 400 μm.

Although there are no particular limitations on the outer diameter of the outer shell layer of the hollow microfiber of the present invention, it is preferably 20 μm to 500 μm.

In one embodiment, the diameter of the hollow portion of the hollow microfiber of the present invention is 5 μm to 200 μm, the inner diameter of the outer shell layer is 10 μm to 400 μm, and the outer diameter of the outer shell layer is 20 μm to 500 μm.

The diameter of the hollow portion and the inner and outer diameters of the outer shell layer of the aforementioned hollow microfiber are, for example, measured values from images obtained with a phase-contrast microscope, and are represented as the average value of measured values obtained at several locations on the microfiber.

Although there are no particular limitations thereon, the length of the hollow microfiber of the present invention is preferably 1 mm to 100 cm and more preferably 5 mm to 20 cm.

The cell-adhesive layer that composes the hollow microfiber of the present invention contains a base material in the form of a cell-adhesive hydrogel. There are no particular limitations on the cell-adhesive hydrogel provided that it allows the formation of a cell layer by allowing the cells to be adhered on the hydrogel followed by culturing the cells, and is able to have adequate permeability to cell culture medium components. In the case of using the microfiber of the present invention for transplantation, the cell-adhesive hydrogel is able to replace body tissue over a long period of time by being decomposed or remodeled by the body's cells.

The cell-adhesive hydrogel is preferably a hydrogel that has been gelled by an external stimulus. The external stimulus is a stimulus that occurs under physiological conditions and/or a stimulus that does not have cytotoxicity, and examples thereof include, but are not limited to, addition of metal ions (such as calcium ions), addition of enzyme, pH change, heating, UV irradiation and radiation exposure.

The cell-adhesive hydrogel is preferably an extracellular matrix component. Alternatively, the cell-adhesive hydrogel of the present invention is preferably selected from the group consisting of chitosan gel, collagen gel, gelatin, peptide gel, laminin gel, fibrin gel and mixtures thereof. Among these, chitosan gel, collagen gel, gelatin, peptide gel and laminin gel are gelled by changing temperature, pH or salt concentration. Fibrin gel is gelled by allowing fibrinogen which is a monomer to act with thrombin which is an enzyme.

In the preparation of the cell-adhesive layer, a hydrophilic organic solvent having a water-miscible property, for example, ethanol, acetone, ethylene glycol, propylene glycol, glycerol, dimethylformamide, and dimethylsulfoxide, may be added. In order to increase the strength of the hydrogel, an appropriate ingredient or a solvent can also be blended. From such a point of view, for example, it is also possible to add dimethyl sulfoxide as a solvent for the preparation of polyvinyl alcohol hydrogel.

One or more biogenic substances such as cells, proteins, lipids, saccharides, nucleic acids, and antibodies may be added to the cell-adhesive layer. The type of the cells is not particularly limited, and examples include, for example, ES cells and iPS cells having pluripotency, various kinds of stem cells having multipotency (hematopoietic stem cells, neural stem cells, mesenchymal stem cells and the like), stem cells having unipotency (liver stem cells, reproduction stem cells and the like), as well as various kinds of differentiated cells, for example, myocytes such as skeletal muscle cells and cardiac muscle cells, nerve cells such as cerebral cortex cells, fibroblasts, epithelium cells, hepatocytes, pancreatic β-cells, skin cells, and the like. The cell-adhesive layer may contain cell culture obtained by culturing cells in the cell-adhesive layer. However, the cells and biogenic substances are not limited to those exemplified above. Various kinds of growth factors suitable for culture of the aforementioned cells, maintenance and proliferation of the cells, or functional expression of the cells, for example, epidermal growth factor (EGF), platelet-derived growth factor (PDGF), transforming growth factor (TGF), insulin-like growth factor (IGF), fibroblast growth factor (FGF), nerve growth factor (NGF), and the like, may be added to the cell-adhesive layer. When a growth factor is used, an appropriate concentration can be chosen according to the type of the growth factor. Further, a non-biogenic substance may be added to the cell-adhesive layer. For example, it is also possible to add fibers such as carbon nanofibers, inorganic substances such as catalytic substances, beads covered with antibodies, or artifacts such as microchips.

The hollow microfiber of the present invention has one or more cell-adhesive layers. Each cell-adhesive layer is present in a continuously laminated state. The constituents of each cell-adhesive layer may be the same or different. Although there are no particular limitations on the number of cell-adhesive layers, it is preferably 1 to 5 layers and more preferably 1 to 3 layers. In one embodiment of the present invention, the number of adhesive-cell layers is one layer.

Although there are no particular limitations thereon, the thickness of the cell-adhesive layer is preferably 10 μm to 250 μm. In addition, the cell-adhesive layer normally has a substantially uniform thickness. Preferably, the cell-adhesive layer has thickness uniformity within the range of ±5%. This thickness uniformity is measured with, for example, a phase-contrast microscope, and is calculated as a percentage of variation with respect to the average of measured values of thickness of the cell-adhesive layer obtained at several locations on the microfiber.

The outer shell layer that composes the hollow microfiber of the present invention contains a base material in the form of a high-strength hydrogel. There are no particular limitations on the high-strength hydrogel provided that it is a hydrogel that has higher mechanical strength than the cell-adhesive layer to be covered and is able to have adequate permeability to cell culture medium components. Gel mechanical strength can be determined in accordance with a method known among persons with ordinary skill in the art, such as by measuring tensile strength or load strength by a method such as using a tensile tester in water. Biological components or non-biological components can also be added to the high-strength hydrogel as necessary.

The high-strength hydrogel is preferably a hydrogel that is gelled by an external stimulus. Examples of external stimuli include, but are not limited to, the addition of metal ions (such as calcium ions), enzyme treatment, pH change, heating, UV irradiation and radiation exposure. In addition, the external stimulus used to form the high-strength hydrogel may be the same as or different from the external stimulus used to form the cell-adhesive hydrogel. Preferably, the external stimuli are respectively different.

The high-strength hydrogel is preferably a hydrogel that can be removed from the microfiber of the present invention by a chemical reaction or enzymatic reaction and the like following formation of the microfiber.

The high-strength hydrogel is more preferably an alginate gel or agarose gel. Alginate gel can be gelled by the addition of calcium ions, and can be removed by enzyme treatment using alginate lyase and the like or by removing the calcium ions by allowing a chelating agent such as EDTA to act at an appropriate concentration. In addition, agarose gel can be gelled by heating and can be removed by enzyme treatment.

Although there are no particular limitations thereon, the thickness of the outer shell layer is preferably 5 μm to 250 μm. In addition, the outer shell layer normally has a substantially uniform thickness. Preferably, the outer shell layer has thickness uniformity within the range of ±5%. This thickness uniformity is measured with, for example, a phase-contrast microscope, and is calculated as a percentage of variation with respect to the average of measured values of thickness of the outer shell layer obtained at several locations on the microfiber.

The composition of constituents of the cell-adhesive layer may be the same or different at any arbitrary location of that layer. For example, in the case of sectioning a tube of the cell-adhesive layer in the axial direction so as to include the central axis thereof, the cell-adhesive layer may be formed so that, although the constituent components may be the same between one cell-adhesive layer and the other cell-adhesive layer, the concentrations of those constituent components differ. In this manner, a tubular structure having anisotropy can be formed, in which portions having different properties are present within a single cell-adhesive layer, by patterning the cell-adhesive layer. Similarly, the composition of constituents of the outer shell layer may be the same or different at any arbitrary location of that layer. For example, in the case of sectioning a tube of the outer shell layer in the axial direction so as to include the central axis thereof, the outer shell layer may be formed so that, although the constituent components may be the same between one outer shell layer and the other outer shell layer, the concentrations of those constituent components differ.

The combination of cell-adhesive hydrogel and high-strength hydrogel used in the hollow microfiber of the present invention is preferably such that the cell-adhesive hydrogel is collagen gel and the high-strength hydrogel is an alginate gel.

There are no particular limitations on the type of cells in the cell layer that composes the hollow microfiber of the present invention provided that they are cells that can adhere to the cell-adhesive layer and be cultured. The cells are preferably cells having the ability to compose a luminal structure in the body such as vascular endothelial cells, lymphatic endothelial cells or renal tubular cells.

The cell layer that composes the hollow microfiber of the present invention is preferably a single layer of cell layer.

The cell-adhesive layer that composes the hollow microfiber of the present invention may contain cells that differ from the cells that compose the cell layer. For example, when the cells that compose the cell layer are vascular endothelial cells, a cell-adhesive layer adjacent to the cell layer may contain vascular smooth muscle cells. In this case, a layer composed of vascular smooth muscle cells can be formed so as to cover the outside of the cell layer composed of vascular endothelial cells.

One aspect of the present invention is a microfiber in which the hollow portion of the hollow microfiber of the present invention is filled with a suspension of cells that compose the cell layer. Although there are no particular limitations on the suspension provided that it does not have cytotoxicity, it is preferably prepared by suspending cells in a liquid selected from the group consisting of polyethylene glycol, glycerol, alginate ester, dextran and mixtures thereof.

One aspect of the present invention is a hollow microfiber that is obtainable by removing the outer shell layer from the hollow microfiber of the present invention. In addition, another embodiment of the present invention is a microfiber obtainable by removing the outer shell layer from a microfiber in which the hollow portion of the hollow microfiber of the present invention is filled with a suspension of cells that compose the cell layer. For example, after producing the microfiber of the present invention by using alginate gel as the high-strength hydrogel and using collagen gel as the cell-adhesive hydrogel, by then subjecting to treatment using an enzyme such as alginate lyase or removing calcium ions by using a chelating agent such as EDTA with an appropriate concentration, a microfiber can be prepared in which only the outer shell layer containing alginate gel has been removed.

For example, the microfiber of the present invention can be sucked into a silicone tube and stored in a state that the gel is stretched along the longitudinal direction of the tube. It is generally difficult to maintain a gelled microfiber in a linear shape when the gelled microfiber is stored in water, buffer, or the like. However, when the microfiber is put into an aqueous medium such as water and buffer, and sucked through a silicone tube having an internal diameter of about 100 μm to several millimeters, of which one end is immersed in the aqueous medium, the microfiber is sucked into the silicone tube from an end thereof in a state that the microfiber is stretched along the longitudinal direction of the tube. The gel can be stored in this state, and upon use, the silicone tube can be cut in an appropriate length to prepare the gel of a desired length. For the storage, appropriate agents such as preservative, pH modifier and buffering agent can be added to the medium in the tube, as required.

One aspect of the present invention is a method for producing a microfiber comprising: (1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, (3) a cell layer that covers the inner periphery of the cell-adhesive layer located closest to the central axis among the one or more cell-adhesive layers, and (4) a cell suspension that fills a hollow portion, comprising the following steps:

(i) forming a laminar flow of the cell suspension, (ii) forming one or more laminar flows of solutions for preparing the cell-adhesive hydrogel that cover the outer periphery of the laminar flow of the cell suspension, (iii) forming a laminar flow of a solution for preparing a high-strength hydrogel that covers the outer periphery of the laminar flow of the solution for preparing the cell-adhesive hydrogel located farthest from the central axis among the laminar flows of the solutions for preparing the cell-adhesive hydrogel, (iv) gelling the solution for preparing the high-strength hydrogel to form an outer shell layer that contains the high-strength hydrogel, (v) gelling the solutions for preparing the cell-adhesive hydrogel to form the one or more cell-adhesive layers containing the cell-adhesive hydrogel, and (vi) culturing the cells in the cell suspension to form the cell layer.

The aforementioned method for producing a microfiber can be carried out using a coaxial microfluidic device provided with a line for introducing the cell suspension, one or more lines for introducing solutions for preparing the cell-adhesive hydrogel that is coaxial to the line for introducing the cell suspension, a line for introducing the solution for preparing the high-strength hydrogel that is coaxial to the line for introducing the cell suspension and the one or more lines for introducing solutions for preparing the cell-adhesive hydrogel, a region for gelling the solution for preparing the high-strength hydrogel, and a region for gelling the solutions for preparing the cell-adhesive hydrogel.

Figure 5:
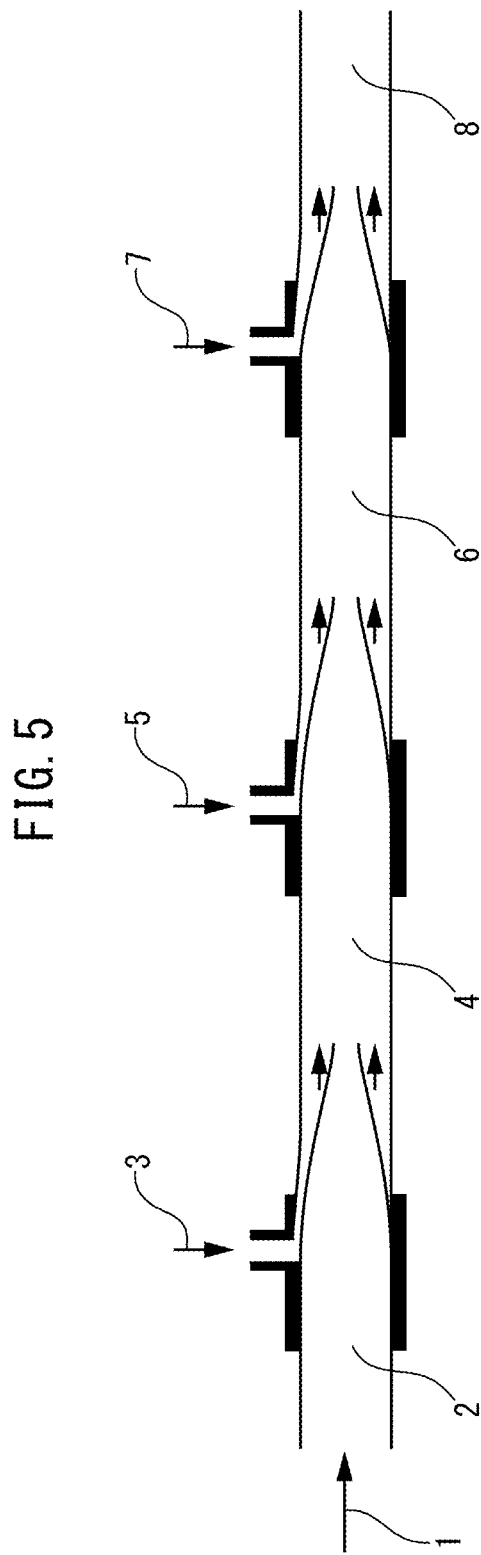
FIG. 5 is a drawing indicating a schematic diagram of a method for producing the microfiber of the present invention having a single cell-adhesive layer using a triple coaxial laminar flow device.
Figure 6:
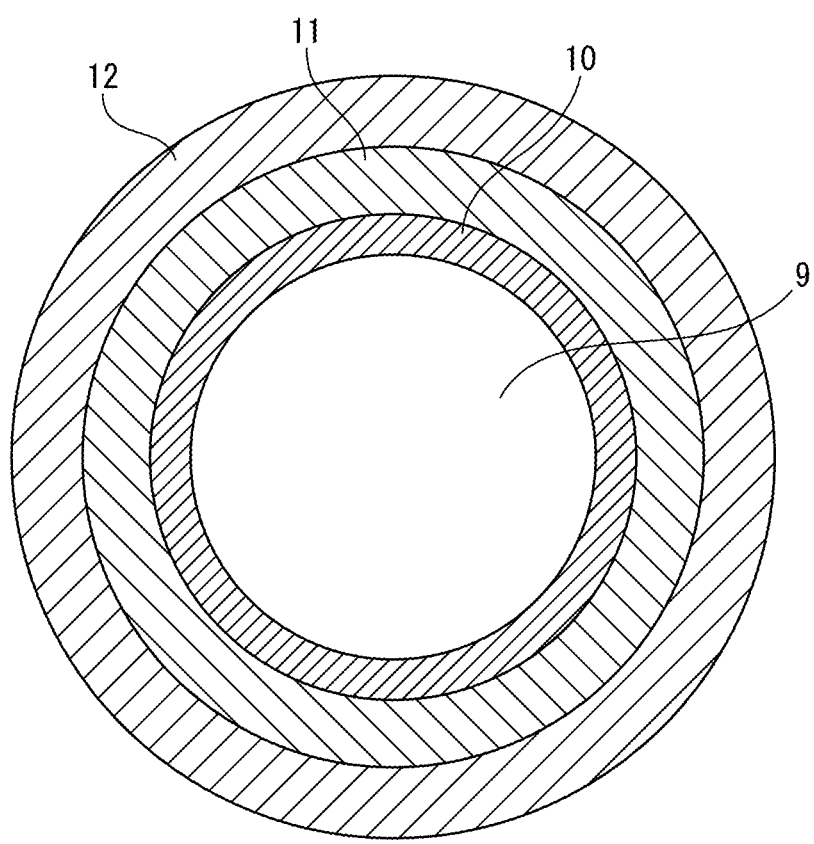
FIG. 6 is a cross-sectional view of a microfiber produced using the laminar flow device of FIG. 5.

FIG. 5 is a drawing indicating a schematic diagram of one example of the method for producing a microfiber of the present invention having a single cell-adhesive layer using a triple coaxial laminar flow device. A cell suspension 1 is injected from a line for introducing the cell suspension 2 to form a laminar flow, a solution 3 for preparing a cell-adhesive hydrogel is injected from a solution introducing line 4 for preparing a cell-adhesive hydrogel to form a laminar flow of the solution for preparing a cell-adhesive hydrogel that covers the outer periphery of the laminar flow of the cell suspension, and a solution 5 for preparing a high-strength hydrogel is injected from a solution introducing line 6 for preparing a high-strength hydrogel to form a laminar flow of the solution for preparing the high-strength hydrogel that covers the outer periphery of the laminar flow of the solution for preparing the cell-adhesive hydrogel. An aggregate of the laminar flows formed is passed through a region 8 for gelling the solution for preparing the cell-adhesive hydrogel and the solution for preparing the high-strength hydrogel, and the solution for preparing the cell-adhesive hydrogel and the solution for preparing the high-strength hydrogel are respectively gelled. For example, gelling can be carried out by introducing the aggregate of the laminar flows formed into a gelling agent solution 7 and/or by applying another external stimulus. Cells are then cultured in the resulting microfiber to form a cell layer that covers the inner periphery of the cell-adhesive layer. FIG. 6 shows a cross-sectional view of a microfiber obtained using the device of FIG. 5.

Although there are no particular limitations on the materials of the line for introducing the cell suspension, line for introducing a solution for preparing the cell-adhesive hydrogel and line for introducing a solution for preparing the high-strength hydrogel, examples thereof include glass, silicone rubber, polymeric resin, metal and ceramics. Although there are no particular limitations thereon, the inner diameter thereof is, for example, 1 mm to 10 mm.

A microfiber of the present invention having two or more cell-adhesive layers can be produced by, for example, providing a line for introducing a solution preparing an additional cell-adhesive hydrogel between the line 4 for introducing a solution for preparing a cell-adhesive hydrogel and the line 6 for introducing a solution for preparing a high-strength hydrogel shown in FIG. 5, injecting the solution for preparing the cell-adhesive hydrogel therefrom, and forming a laminar flow of the solution for preparing the cell-adhesive hydrogel that covers the outer periphery of the laminar flow of the solution for preparing the cell-adhesive hydrogel formed by injection from the line for introducing the solution for preparing the cell-adhesive hydrogel arranged immediately prior thereto.

There are no particular limitations on the liquid in which the cells are suspended provided that it does not have cytotoxicity, and that it has viscosity that enables the laminar flow of the solution for preparing the adhesive-cell hydrogel to be formed so as to cover the outer periphery of the laminar flow of the cell suspension. A liquid having a viscosity of about 10 cP to 500 cP is preferable. More preferably, the liquid in which the cells are suspended is a liquid selected from the group consisting of polyethylene glycol, glycerol, alginate ester, dextran and mixtures thereof.

There are no particular limitations on cell density in the cell suspension provided that it allows cells to be uniformly cultured on the cell-adhesive layer in the resulting microfiber. Cell density is preferably $1.0 \times 10^6$ cells/mL to $5.0 \times 10^8$ cells/mL and more preferably $1.0 \times 10^6$ cells/mL to $1.0 \times 10^8$ cells/mL.

It is necessary to adjust the viscosity and flow rate of each solution during the course of producing the microfiber of the present invention so that each solution forms a laminar flow. In the present description, "laminar flow" refers to a flow in which the streamline of a fluid is parallel to the direction in which the fluid is injected. In addition, two "laminar flows" of adjacent fluids are not mutually mixed, and the streamline thereof are maintained in a regular form.

Reynolds number is used as an indicator of laminar flow formation. Reynolds number is represented by the following equation:

$$Re = vL/\nu \qquad \text{[Equation 1]}$$

(wherein, v represents flow rate (m/sec), L represents a representative length (m), and $\nu$ represents the coefficient of kinematic viscosity ($m^2$/sec)).

In the method of the present invention, there are no particular limitations on the Reynolds numbers of the flows of each of the cell suspension, solution for preparing cell-adhesive hydrogel and solution for preparing high-strength hydrogel provided that they are values sufficient for being able to form laminar flow. For example, a laminar flow can be formed for each of these liquids when their Reynolds numbers are 2000 or less.

Gelling of the solution for preparing the high-strength hydrogel and solution for preparing the cell-adhesive hydrogel is carried out by applying an external stimulus. Preferably, the external stimulus is applied in a region for gelling the solution for preparing the high-strength hydrogel and a region for gelling the solution for preparing the cell-adhesive hydrogel, respectively. The region for gelling the solution for preparing the high-strength hydrogel and the region for gelling the solution for preparing the cell-adhesive hydrogel may be the same or different. Examples of external stimuli include, but are not limited to, the addition of metal ions (such as calcium ions), addition of enzyme, pH change, heating, UV irradiation and radiation exposure. Gelling conditions for the cell-adhesive hydrogel and high-strength hydrogel may be the same or different. Preferably, gelling is carried out under different conditions. For example, in the case the solution for preparing the cell-adhesive hydrogel is a collagen solution, the solution is gelled to form a collagen gel by heating for several minutes to one hour at about 37° C. In addition, in the case the solution for preparing the high-strength hydrogel is a sodium alginate solution, the solution is gelled to form an alginate gel by passing a laminar flow of the sodium alginate solution through an aqueous solution containing metal ions such as calcium ions (such as an aqueous calcium chloride solution), which is a gelling agent solution. Preferably, gelling of the solution for preparing the high-strength hydrogel is carried out more rapidly than gelling of the solution for preparing the cell-adhesive hydrogel. As a result, the solution for preparing the cell-adhesive hydrogel can be prevented from diffusing to the outside rather than the outer shell layer.

The composition of constituents of the formed cell-adhesive layer may be the same or different at any arbitrary location on the layer. For example, in the case of sectioning a tube of the cell-adhesive layer in the axial direction so as to include the central axis thereof, although the constituent components may be the same between one cell-adhesive layer and the other cell-adhesive layer, the concentrations of those constituent components differ. In this manner, a tubular structure having anisotropy can be formed, in which portions having different properties are present within a single cell-adhesive layer, by patterning the cell-adhesive layer. This type of tubular structure can be fabricated by, for example, forming laminar flows of these solutions so that the concentration of the solution for preparing a cell-adhesive hydrogel for forming one cell-adhesive layer and the concentration of the solution for preparing a cell-adhesive hydrogel for forming the other cell-adhesive layer are different. Similarly, the composition of constituents of the outer shell layer may be the same or different at any arbitrary location of that layer. For example, in the case of sectioning a tube of the outer shell layer in the axial direction so as to include the central axis thereof, the outer cell layer may be formed so that, although the constituent components may be the same between one outer shell layer and the other outer shell layer, the concentrations of those constituent components differ. This type of tubular structure can be fabricated by, for example, forming laminar flows of these solutions so that the solution for preparing a high-strength hydrogel for forming one outer shell layer and the solution for preparing a high-strength hydrogel for forming the other outer shell layer have different concentrations.

After gelling the solution for preparing the high-strength hydrogel and the solution for preparing the cell-adhesive hydrogel, cells introduced into the hollow portion of the microfiber in the form of a cell suspension are cultured, and a cell layer is formed that covers the inner periphery of the cell-adhesive layer located closest to the central axis. Culturing is carried out by, for example, directly immersing the resulting microfiber in a cell culture medium. In this case, nutrient components contained in the cell culture medium are able to pass through the outer shell layer and cell-adhesive layer by diffusion. Although there are no limits on cell culturing conditions, culturing is carried out, for example, for 24 to 72 hours at 37° C.

According to the method for producing a microfiber of the present invention, a microfiber capable of transporting a liquid can be produced, which have a constant length (of, for example, 0.5 cm to 100 cm), and in which a continuous luminal structure has been formed by a cell layer. The cell-adhesive layer and outer shell layer that form the microfiber have a substantially uniform thickness.

One aspect of the present invention is a kit for carrying out the aforementioned method for producing a microfiber, comprising: (i) a solution for preparing a cell-adhesive hydrogel that forms a cell-adhesive hydrogel by gelling, (ii) a solution for preparing a high-strength hydrogel that forms a high-strength hydrogel by gelling, (iii) a cell suspension, and (iv) a manual for producing the microfiber.

One aspect of the present invention is a method for producing a hollow microfiber comprising: (1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, and (3) a cell layer that covers the inner periphery of the cell-adhesive layer located closest to the central axis among the one or more cell-adhesive layers. This type of hollow microfiber can be produced by removing a cell suspension from a microfiber produced according to the aforementioned method comprising (1) one or more cell-adhesive layers containing a cell-adhesive hydrogel, (2) an outer shell layer containing a high-strength hydrogel that covers the outer periphery of the cell-adhesive layer located farthest from the central axis among the one or more cell-adhesive layers, (3) a cell layer that covers the inner periphery of the cell-adhesive layer located closest to the central axis among the one or more cell-adhesive layers, and (4) a cell suspension that fills a hollow portion. Although there are no particular limitations on the method used to remove the cell suspension, the cell suspension can be removed by, for example, pumping a liquid other than the cell suspension into the hollow portion.

Conventionally known artificial blood vessels are, for example, tubes made of a synthetic polymer and are associated with the problems of constriction and material deterioration by thrombi formed after transplantation. On the other hand, since the hollow microfiber of the present invention produced using vascular endothelial cells is composed of vascular components, the risk of thrombus formation is expected to be extremely low in comparison with artificial vessels produced from artificial materials. In addition, since the hollow microfiber of the present invention is composed of biological components, once it becomes connected to body tissue, it is thought to be gradually replaced by divided cells or recipient cells after transplant, thereby reducing the need for replantation. Moreover, a new vascular network can be formed autonomously corresponding to the internal environment in the vicinity of the transplant site.

In addition, although the microfiber of the present invention can be used in transplant applications in the field of regenerative medicine, it is not limited to these applications. For example, the microfiber of the present invention can also be applied to drug screening by constructing a model such as a pharmacokinetics model, in vitro model of metastasis or in vitro model of thrombus formation using the microfiber of the present invention and three-dimensional tissue fabricated using this microfiber.

EXAMPLES

Although the following provides a more detailed explanation of the present invention with reference to the examples and comparative examples indicated below, it goes without saying that the present invention is not limited by these examples.

Comparative Example 1

Production of Microfiber Composed of Core Portion Containing Collagen Gel and Vascular Endothelial Cells and Shell Portion Containing Alginate Gel that Covers the Core Portion A microfiber was produced according to the method described in Non-Patent Document 1 using a triple coaxial laminar flow device. When the microfiber was cultured, although a cell layer composed of vascular endothelial cells formed spontaneously, the cell layer was formed randomly and a continuous luminal structure was unable to be formed.

Example 1

(a) Production of Microfiber Comprising Cell-Adhesive Layer Containing Collagen Gel, Outer Shell Layer Containing Alginate Gel that Covers the Cell-Adhesive Layer, and Vascular Endothelial Cell Layer Covering the Cell-Adhesive Layer A microfiber was produced using the device shown in FIG. 5. A polyethylene glycol solution of vascular endothelial cells ($2.0 \times 10^7$ cells/mL) was prepared as a cell suspension 1, and the cell suspension 1 was injected from a line for introducing the cell suspension 2 at a flow rate of 10 μL/min to form a laminar flow of the solution. An aqueous collagen solution (4 mg/ml) was prepared as a solution 3 for preparing a cell-adhesive hydrogel, and the aqueous collagen solution was injected from a line 4 for introducing a solution for preparing a cell-adhesive hydrogel at a flow rate of 200 μl/min to form a laminar flow of the aqueous collagen solution that covered the outer periphery of the laminar flow of the cell suspension. An aqueous sodium alginate solution (1.5 g/ml) was prepared as a solution 5 for preparing a high-strength hydrogel, and the aqueous sodium alginate solution was injected from a line 6 for introducing a solution for preparing a high-strength hydrogel at a flow rate of 125 μl/min to form a laminar flow of the aqueous sodium alginate solution that covered the outer periphery of the laminar flow of the aqueous collagen solution. An aggregate of the resulting laminar flows was gelled in a region 8 for gelling the solution for preparing the high-strength hydrogel and the solution for preparing the cell-adhesive hydrogel. More specifically, an aqueous calcium chloride solution (100 mM, flow rate: 2500 μl/min) which is a gelling agent solution 7 was introduced followed by heating for 15 minutes at 37° C. to produce a microfiber (inner diameter of outer shell layer: 270 μm, outer diameter of outer shell layer: 350 μm, thickness of collagen layer: 100 μm, and each of these values was calculated as the average value of measured values from images obtained with a phase-contrast microscope). A single layer of a vascular endothelial cell layer that uniformly covered the inner periphery of the collagen layer was formed by culturing the cells in the resulting microfiber.

(b) Dissolution of Outer Shell Layer

The alginate gel of the outer shell layer was dissolved by allowing alginate lyase to act on the microfiber obtained in (a) (FIG. 2).

Example 2

Production of Microfiber Comprising Cell-Adhesive Layer Containing Vascular Smooth Muscle Cells, Outer Shell Layer Containing Alginate Gel that Covers Outer Periphery of the Cell-Adhesive Layer, and Vascular Endothelial Cell Layer Covering Inner Periphery of the Cell-Adhesive Layer A microfiber was obtained in the same manner as Example 1 with the exception of preparing an aqueous collagen solution (4 mg/ml) containing vascular smooth muscle cells ($1.25 \times 10^6$ cells/mL) as the solution 3 for preparing a cell-adhesive hydrogel, and injecting from the line 4 for introducing a solution for preparing a cell-adhesive hydrogel at a flow rate of 200 μl/min to form a laminar flow of the aqueous collagen solution that covered the outer periphery of laminar flow of the cell suspension (inner diameter of outer shell layer: 270 μm, outer diameter of outer shell layer: 350 μm, thickness of collagen layer: 100 μm, and each of these values was calculated as the average value of measured values from images obtained with a phase-contrast microscope). A microfiber was obtained in which a vascular smooth muscle cell layer was laminated on the outside of a single layer of the vascular endothelial cell layer by culturing the cells in the resulting microfiber (FIG. 3).

Example 3

Liquid was pumped into the hollow portion of the microfiber obtained in Example 1 by clamping the microfiber between narrowed glass tubes. When liquid was pumped at a flow rate of 1 μL/min using a syringe pump, liquid was able to be pumped into the resulting hollow portion of the vascular endothelium layer. When a dispersion of polystyrene beads having a diameter of 5 μm was pumped into the hollow portion, the beads were confirmed with a light microscope to have migrated to the hollow portion accompanying pumping (refer to upper image (t=0 seconds) and lower image (t=18 seconds) of FIG. 4 in which polystyrene beads are indicated with arrows).

INDUSTRIAL APPLICABILITY

The hollow microfiber of the present invention can be preferably used as an alternative to luminal structures in the body such as blood vessels or lymph ducts.

BRIEF DESCRIPTION OF THE REFERENCE SYMBOLS

1 Cell suspension
2 Line for introducing the cell suspension
3 Solution for preparing cell-adhesive hydrogel
4 Line for introducing the solution for preparing cell-adhesive hydrogel
5 Solution for preparing high-strength hydrogel
6 Line for introducing the solution for preparing high-strength hydrogel
7 Gelling agent solution
8 Region for gelling solution for preparing high-strength hydrogel and solution for preparing cell-adhesive hydrogel
9 Hollow portion
10 Cell layer
11 Cell-adhesive layer
12 Outer shell layer

The invention claimed is:

1. A hollow microfiber, comprising:
   (1) one or more cell-adhesive layers containing a cell-adhesive hydrogel,
   (2) an outer shell layer containing a high-strength hydrogel that covers the outer periphery of the cell-adhesive layer located farthest from the central axis among the one or more cell-adhesive layers, and
   (3) a cell layer that covers the inner periphery of the cell-adhesive layer located closest to the central axis among the one or more cell-adhesive layers,
   wherein the one or more cell-adhesive layers have a substantially uniform thickness.

2. The hollow microfiber according to claim 1, wherein the cell-adhesive hydrogel is selected from the group consisting of chitosan gel, collagen gel, gelatin, peptide gel, laminin gel, fibrin gel and mixtures thereof.

3. The hollow microfiber according to claim 1, wherein the high-strength hydrogel is an alginate gel or agarose gel.

4. The hollow microfiber according claim 1, wherein the outer diameter of the outer shell layer is 20 μm to 500 μm.

5. The hollow microfiber according to claim 1, wherein the cells that compose the cell layer are selected from the group consisting of vascular endothelial cells, lymphatic endothelial cells and renal tubular cells.

6. The hollow microfiber according to claim 1, wherein at least one of the one or more cell-adhesive layers further contains cells differing from the cells of the cell layer.

7. The hollow microfiber according to claim 1, wherein the number of the one or more cell-adhesive layers is one layer.

8. A microfiber in which the hollow portion of the hollow microfiber according to claim 1 is filled with a suspension of the cells that compose the cell layer.

9. A hollow microfiber obtainable by removing the outer shell layer from the hollow microfiber according to claim 1.

10. A microfiber obtainable by removing the outer shell layer from the microfiber according to claim 1.

11. A method for producing a microfiber comprising:
   (1) one or more cell-adhesive layers containing a cell-adhesive hydrogel,
   wherein the one or more cell-adhesive layers have a substantially uniform thickness,
   (2) an outer shell layer containing a high-strength hydrogel that covers the outer periphery of the cell-adhesive layer located farthest from the central axis among the one or more cell-adhesive layers,
   (3) a cell layer that covers the inner periphery of the cell-adhesive layer located closest to the central axis among the one or more cell-adhesive layers, and
   (4) a cell suspension that fills a hollow portion; wherein, the method comprises the following steps:
   (i) forming a laminar flow of the cell suspension,
   (ii) forming one or more laminar flows of solutions for preparing the cell-adhesive hydrogel that cover the outer periphery of the laminar flow of the cell suspension,
   (iii) forming a laminar flow of a solution for preparing a high-strength hydrogel that covers the outer periphery of the laminar flow of the solution for preparing the cell-adhesive hydrogel located farthest from the central axis among the laminar flows of the solutions for preparing the cell-adhesive hydrogel,
   (iv) gelling the solution for preparing the high-strength hydrogel to form an outer shell layer that contains the high-strength hydrogel,
   (v) gelling the solutions for preparing the cell-adhesive hydrogel to form the one or more cell-adhesive layers containing the cell-adhesive hydrogel, and
   (vi) culturing the cells in the cell suspension to form the cell layer.

12. The method according to claim 11, wherein
   the method uses a coaxial microfluidic device provided with:
   a line for introducing the cell suspension,
   one or more lines for introducing solutions for preparing the cell-adhesive hydrogel that are coaxial to the line for introducing the cell suspension,
   a line for introducing a solution for preparing the high-strength hydrogel that is coaxial to the line for introducing the cell suspension and the one or more lines for introducing the solutions for preparing the cell-adhesive hydrogel, a region for gelling the solution for preparing the high-strength hydrogel, and a region for gelling the solutions for preparing the cell-adhesive hydrogel; and, the method comprises the following steps:

(i) forming a laminar flow of the cell suspension by injecting the cell suspension from the line for introducing the cell suspension, ( ii) forming one or more laminar flows of the solutions for preparing the cell-adhesive hydrogel that cover the outer periphery of the laminar flow of the cell suspension by injecting the solutions for preparing the cell-adhesive hydrogel from the one or more lines for introducing the solution for preparing the cell-adhesive hydrogel, (iii) forming a laminar flow of the solution for preparing the high-strength hydrogel that covers the outer periphery of the laminar flow of the solution for preparing the cell-adhesive hydrogel located farthest from the central axis among the one or more laminar flows of the solutions for preparing the cell-adhesive hydrogel by injecting the solution for preparing the high-strength hydrogel from the line for introducing the solution for preparing the high-strength hydrogel, (iv) gelling the solution for preparing the high-strength hydrogel by passing an aggregate of the laminar flows formed in steps (i) to (iii) through the region for gelling the solution for preparing the high-strength hydrogel to form the outer shell layer containing the high-strength hydrogel, (v) gelling the solutions for preparing the cell-adhesive hydrogel by passing an aggregate of the laminar flows formed in steps (i) to (iii) through the region for gelling the solutions for preparing the cell-adhesive hydrogel to form cell adhesive layers containing the cell-adhesive hydrogel, wherein this step is carried out before or after step (iv) or simultaneous to step (iv), and (vi) culturing the cells in the cell suspension to form the cell layer.

13. The method for producing the microfiber according to claim 11, wherein the cell density in the cell suspension is $1.0 \times 10^6$ cells/ml to $1.0 \times 10^8$ cells/mL.

14. The method for producing the microfiber according to claim 11, wherein the solution for preparing the cell-adhesive hydrogel and the solution for preparing the high-strength hydrogel are gelled under different conditions.

15. The method for producing the microfiber according to claim 11, wherein the cell-adhesive hydrogel is selected from the group consisting of chitosan gel, collagen gel, gelatin, peptide gel, laminin gel, fibrin gel and mixtures thereof.

16. The method for producing the microfiber according to claim 11, wherein the high-strength hydrogel is an alginate gel or agarose gel.

17. The method for producing the microfiber according to claim 11, wherein the cell-adhesive hydrogel is a collagen gel and the high-strength hydrogel is an alginate gel.

* * * * *